United States Patent [19]

Haaga

[11] Patent Number: 5,080,655
[45] Date of Patent: * Jan. 14, 1992

[54] MEDICAL BIOPSY NEEDLE

[76] Inventor: John R. Haaga, 3409 N. Hilltop, Chagrin Falls, Ohio 44022

[*] Notice: The portion of the term of this patent subsequent to Jun. 13, 2006 has been disclaimed.

[21] Appl. No.: 514,769

[22] Filed: Apr. 26, 1990

Related U.S. Application Data

[60] Division of Ser. No. 288,858, Dec. 23, 1988, Pat. No. 4,936,835, which is a continuation-in-part of Ser. No. 199,130, May 26, 1988, Pat. No. 4,838,280.

[51] Int. Cl.⁵ .............................................. A61M 5/32
[52] U.S. Cl. ...................... 604/265; 128/754
[58] Field of Search .................. 128/760, 751, 754; 604/265, 270

[56] References Cited

U.S. PATENT DOCUMENTS

| | | | |
|---|---|---|---|
| 2,603,217 | 7/1952 | McShirley | 128/239 |
| 2,691,373 | 10/1954 | Bried | 128/239 |
| 2,814,296 | 11/1957 | Everett | 128/339 |
| 3,106,483 | 10/1963 | Kline et al. | 117/62.2 |
| 3,358,684 | 12/1967 | Marshall | 128/214.4 |
| 3,396,727 | 8/1968 | Mount | 128/349 |
| 3,736,939 | 7/1973 | Taylor | 128/349 B |
| 4,306,563 | 12/1981 | Iwatschenko | 128/349 R |
| 4,396,021 | 8/1983 | Baumgartner | 128/751 |
| 4,564,361 | 1/1986 | Akiyama | 604/265 |
| 4,650,488 | 3/1987 | Bays et al. | 623/12 |
| 4,708,147 | 11/1987 | Haaga | 128/753 |
| 4,710,181 | 12/1987 | Fuqua | 604/280 |
| 4,827,940 | 5/1989 | Mayer et al. | 128/642 |
| 4,838,280 | 6/1989 | Haaga | 128/751 |

Primary Examiner—Max Hindenburg
Attorney, Agent, or Firm—Body, Vickers & Daniels

[57] ABSTRACT

An improved medical needle is disclosed which has a bioabsorbable gelatin cutting or puncturing tip formed therein. The gelatin characteristic renders the needle incapable of penetration after initial use. Additionally, the gelatin partially dissolves to leave a coating on the punctured tissue margin which acts to minimize hemorrhaging complications. Hemorrhaging complications are alternatively addressed by a non-bioabsorbable in situ sheath positioned at the punctured tissue site which compresses the tissue.

5 Claims, 2 Drawing Sheets

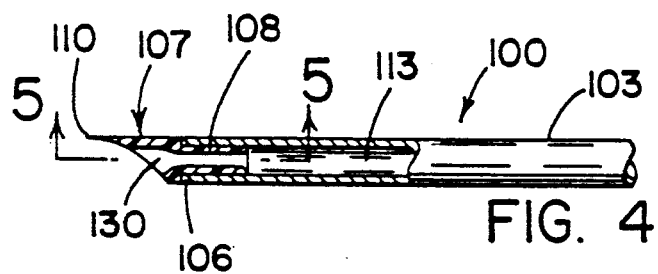
FIG. 4
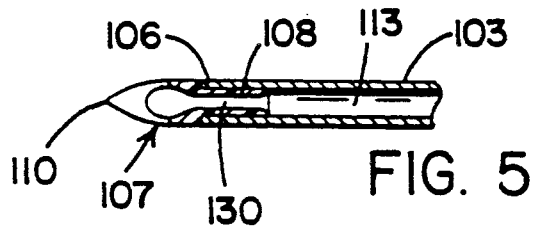
FIG. 5
FIG. 6
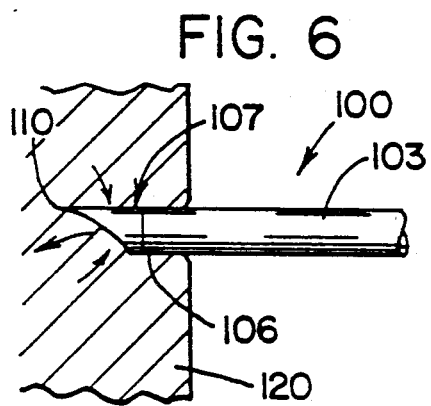
FIG. 7
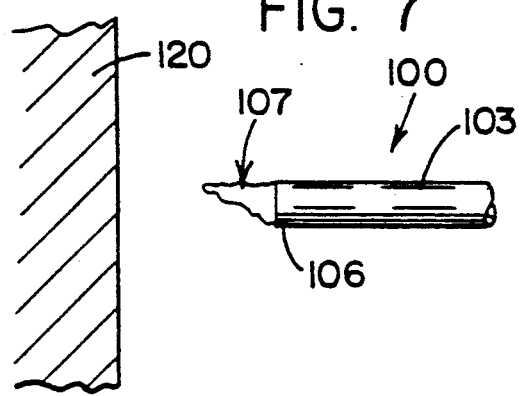
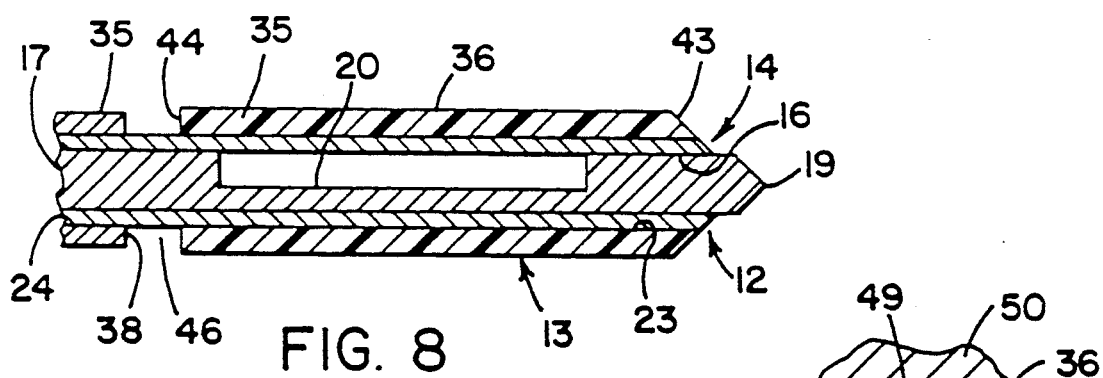
FIG. 8
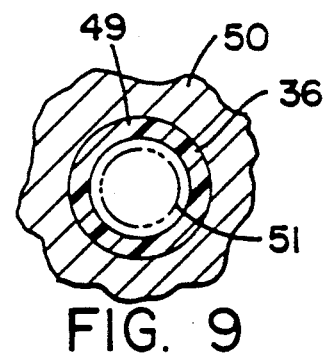
FIG. 9

MEDICAL BIOPSY NEEDLE

This is a division of application Ser. No. 288,858 filed Dec. 23, 1988, now U.S. Pat. No. 4,936,835 which in turn is a continuation-in-part of application Ser. No. 199,130 filed May 26, 1988 now U.S. Pat. No. 4,838,280 dated June 13, 1989.

This invention relates generally to medical needles and more particularly to a needle construction which generally incorporates a bioabsorbable material as a part thereof.

The invention is particularly applicable to biopsy and hypodermic needles and the like and will be described with particular reference thereto. However, it will be appreciated by those skilled in the art that the invention has broader application and in a broad sense is applicable to any instrument for use in any surgical procedure where the patient's tissue must be punctured.

INCORPORATION BY REFERENCE

My patent application, U.S. Ser. No. 199,130 filed May 26, 1988 (hereafter the "parent patent application") in its entirety and including the drawings thereof is incorporated herein by reference. In addition, all references incorporated by reference in my prior patent application are likewise incorporated in their entirety by reference herein. Such material specifically includes as a part and parcel of this specification, U.S. Pat. Nos. 4,708,147 dated Nov. 24, 1987; 3,358,684 dated Dec. 19, 1967 and 3,106,483 dated Oct. 8, 1963.

BACKGROUND

In my prior patent application I disclosed the concept of a bioabsorbable, hemostatic sheath to be used with any suitable mechanism for in situ positioning of the sheath which would prevent hemorrhagic complications arising from the puncturing/cutting operation performed by the surgical instrument to which the sheath was attached. Since that discovery, further experimentation has disclosed further extensions and modifications of the sheath concept which will be subsequently disclosed and also, further adaptations and utilization of the bioabsorbable gelatin material discussed in my prior application.

More specifically, in today's hospital environment used hypodermic needles and the like present a far greater health concern today than in the past. The presence of certain transmittable viruses, diseases, etc. such as AIDS have caused stringent procedures adopted by health professionals to avoid being inadvertently punctured by needles, specifically hypodermic needles, used to provide medication to AIDS inflicted patients. This problem is known to not only affect health professionals, but also drug addicts who typically "share" hypodermic needles and others who simply have to handle the needles during the disposal process. To avoid this, hospitals not only have had to take special precautions concerning the use of the needles and the like by its staff but also have had to take special precautions in the disposal of the needles which are a toxic and/or hazardous waste. Accordingly, there is a definitive need for a medical needle which, after it is initially used to inject medication into the patient, is rendered unusable in the sense that the needle is no longer capable of puncturing the skin.

With respect to the in situ bioabsorbable sheath disclosed in my prior patent application, there are applications where either the organ or tissue punctured by the surgical instrument cannot tolerate the presence of a foreign object (or the presence of a foreign object is not advisable), even a bioabsorbable one. On the other hand, there are other surgical applications which not only can tolerate the presence of a foreign object but which must use the foreign object to provide an access to the organ or the tissue punctured by the needle or surgical instrument. The bioabsorbable sheath cannot provide such an access. While both applications are somewhat unrelated, there is always present hemorrhagic concerns resulting from the puncture of the tissue and/or organ by the needle or surgical instrument.

SUMMARY OF THE INVENTION

It is one of the principal features of the present invention to provide a medical needle or like instrument whose cutting or puncturing edge is rendered incapable of further puncture after initial usage.

This feature is achieved in a medical needle and the like used for injecting a liquid medication into the subcutaneous tissue of a patient where the needle has a cutting tip for puncturing the tissue formed of a bioabsorbable gelatin material which at least partially dissolves after initial use of the needle rendering the needle useless for tissue or skin puncture thereafter. In accordance with one particular feature of the invention, the needle is a hypodermic needle and includes a syringe, a hollow cylinder in communication with the syringe and a removable tip formed of bioabsorbable gelatin material so that the tip remains in the tissue after injection, thus rendering the hypodermic needle incapable of further puncture after use. In accordance with a more specific aspect of the invention, the removable tip has a base portion adjacent to and larger than the distal end of the hollow cylinder. The cutting edge is opposite the base portion and the tip tapers radially outwardly from the cutting edge to the base portion. The tip is generally solid and thus closes the distal end of the hollow cylinder which has apertures or openings extending through the side for escape of the medication. The syringe is effective to force liquid medicant through the hollow cylinder to dislodge the tip therefrom during injection and the shape of the tip is such to insure that the tip remains in the tissue after the needle has been removed.

In accordance with another aspect of the invention, the gelatin material is cast into the distal end of the hollow cylinder, and the tip is then sharpened into a cutting edge and a central hole provided therethrough to establish fluid communication with the hollow cylinder. The tip remains on the metal cylinder when the needle is removed after injection, but because body fluid and medication diluent is absorbed into the tip during injection, the sharp tip becomes soft and nonfunctional as a penetration device. Preferably, after use, the needle is dropped in a water bath which further dissolves the tip making the needle unusable.

In accordance with another aspect of the invention, a biopsy needle or like instrument for taking a biopsy specimen from a patient is provided. The needle has an unactuated position defined by the relative position of its parts prior to insertion in the patient, an actuated position defined by the relative position of its parts while the specimen is being taken and a retracted position defined by the relative position of its parts when the needle is removed from the site where the biopsy was taken. The needle includes an inner cutting cannula having a distal portion for insertion into the site and a contiguous proximal portion extending from the distal portion. The distal portion is defined as that length of the inner cannula which is inserted into the patient in the actuated position and includes means to sever the specimen from the patient. An outer hollow cannula which is coaxial with and receives the inner cannula has a proximal portion and a separable distal portion such that the distal portion is separated from the proximal portion and remains at the site in the retracted position of the needle. Any conventional positioning mechanism such as springs or the like associated with the proximal portions of the inner and the outer cannula may be provided to cause movement of one of the cannulas relative to the other to achieve the aforesaid positions. The distal portion of the outer cannula compresses the tissue of the patient at the site where the specimen was taken and remains at that site and the compression of the tissue is effective to prevent hemorrhaging complications. Specifically, the distal portion or the sheath is constructed of a non-bioabsorbable material such as teflon and the like while remaining at the site to provide access thereto.

In accordance with a still further aspect of the invention, a medical device for insertion at least into the subcutaneous tissue of a patient is provided. The device comprises a hollow cylindrical member having a distal end which is formed into a cutting end and some portion of the cylindrical member comprises a bioabsorbable gelatin material such that when the device is inserted into the tissue, the body fluid and medical diluent acts to soften the bioabsorbable material. When the device is withdrawn from the tissue, a portion of the material is removed or wiped off. The small amount of gelatin remaining at the tissue margin is quite sticky and produces adherence of the margins of the tissue so that leakage of air and/or blood does not occur, thus preventing or tending to prevent hemorrhagic complications. In the hypodermic needle embodiment discussed above, the bioabsorbable cutting end which is permanently affixed to the hollow metal cylinder will leave a small amount of gelatin at the tissue margin to achieve this effect. In the biopsy needle embodiment, the bioabsorbable sheath can be permanently affixed to the proximal portion of the outer cannula and will deposit a small amount of gelatin at the site. In a more general sense, simply coating the hollow metal cylinder of the needle with a bioabsorbable gelatin material will achieve the effect.

It is thus one of the objects of the invention to provide a needle having a bioabsorbable cutting end which upon insertion into the tissue becomes moist thus reducing its coefficient of friction of the substance and rendering the needle more easily penetrable into the tissue.

Yet another object of the invention is to provide a portion of a medical needle with a bioabsorbable gelatin material which material tends to dissolve and become sticky when inserted into the tissue of the patient leaving a small amount of material at the tissue margins of the puncture to avoid hemorrhaging complications.

In accordance with another object of the invention, hemorrhaging complications arising from insertion of a medical needle and the like into a patient are minimized by the position of an in situ, non-bioabsorbable sheath which is effective to compress the tissue at the margins of the puncture.

Still a further object of the invention is to provide a medical needle which is not likely to puncture the subcutneous tissue of a body after it has been initially used.

Yet a still further object of the invention is to provide a needle which alleviates the problems of transmissibility of viruses, diseases and the like, such as AIDS, unintentionally afflicting health professionals, drug addicts, etc. while also addressing the handling concerns present in the waste disposal of such needle.

Still yet another object of the invention is to provide a medical needle which can be easily and economically constructed while effective in operation.

These and other objects of the invention will become apparent to those skilled in the art upon a reading and understanding of the following detailed description of various embodiments of the invention.

BRIEF DESCRIPTION OF THE DRAWINGS

Reference may now be had to the drawings which illustrate various embodiments that the invention may take in physical form and in certain parts and arrangement of parts wherein:

FIG. 4 is a longitudinal, schematic view, partially in section, of a needle similar to FIG. 1 employing an alternative embodiment of the invention;

FIG. 5 is a schematic, partial section view of the needle of FIG. 4 taken along lines 5—5 of FIG. 4;

FIG. 6 is a schematic view of the needle of FIG. 4 shown inserted into the tissue of a patient;

FIG. 7 is a view of the needle of FIG. 4 after it has been withdrawn from the tissue of a patient;

FIG. 8 is a view similar to FIG. 5 of my prior patent application; and

FIG. 9 is a view similar to FIG. 6 of my prior patent application.

DETAILED DESCRIPTION OF THE INVENTION

Figure 1:
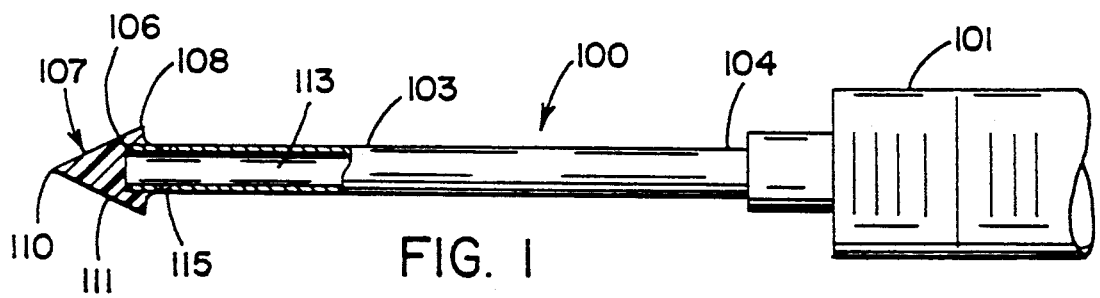
FIG. 1 is a longitudinal, schematic view of a needle, partly in section, embodying the invention.

Referring now to the drawings wherein the showings are for the purpose of illustrating preferred embodiments of the invention only and not for the purpose of limiting the same, reference is first had to FIGS. 8 and 9 which as noted above correspond respectively to FIGS. 5 and 6 of my prior patent application. Because my prior patent application, including the drawings, is incorporated by reference in the specifications hereof, reference numerals for FIGS. 8 and 9 are identical to indicate the same parts, surfaces, etc. which have been described in my prior patent application. Reference to the specifications of my prior patent application should be had for a more detailed explanation of the functioning of the device than that disclosed herein. In this application, reference numeral 36 in FIGS. 8 and 9 designates a removable hemostatic sheath which has a low coefficient of friction and is non-bioabsorbable in nature. For example, teflon or any other suitable plastic having a low coefficient of friction could be used. While non-bioabsorbable, hemostatic sheath 36 could be constructed exactly as shown in FIG. 5 of my prior patent application. For purposes of this specification, I have chosen to show hemostatic sheath 36 as having a slightly larger outside diameter than the proximal portion 35 of outer cannula 13 and also, I have provided, optionally, a conically shaped entry end 43 for hemostatic sheath 36. As discussed in my prior patent application and as shown in FIG. 9, cutting cannula 12 leaves a generally cylindrical void defined by tissue margin 51 (initially shown as the dot-dash line) and when non-bioabsorbable hemostatic sheath 36 is inserted in the void, the margin is expanded to a cylindrical edge shown as 49 and the tissue surrounding the void is compressed. I have discovered that compression of the tissue by means of hemostatic sheath 36 is sufficient to avoid hemorrhaging complications and that a bioabsorbable sheath, while preferred, is not inherently necessary for all applications to prevent hemmorhaging. Optionally, the non-bioabsorbable sheath could be coated with thrombin. In the broad aspects of this feature of the invention, a sheath simply fits over a hollow metal cylinder which can either have a puncturing end or receive a hollow cylinder having a cutting or puncturing end. Any conventional mechanism can be employed to slide the sheath over the hollow metal cylinder so that the sheath is deposited at a site within the patient. In my prior patent application, I showed a hand actuated mechanism. Conventional spring actuated mechanisms can be employed. The sheath compresses the margins of the tissue to alleviate hemorrhaging complications while also providing access to the site for further surgical procedures. After the surgical procedures requiring access to the site are completed, the sheath, being non-bioabsorbable is then removed from the site by any conventional procedure.

In accordance with another aspect of the invention, sheath 36 is bioabsorbable and is not left at the puncture site. This could be accomplished, for example, by simply making the frangible connection shown at 78 in FIG. 7a of my parent patent application non-frangible. Alternatively, and without having reference to a biopsy needle, the medical needle could simply be coated with the bioabsorbable gelatin material or at least the distal penetrating portion of the hollow cylindrical end of a medical needle could be coated or formed with a bioabsorbable gelatin material. In such instances, the gelatin material upon contact with body fluids when the tissue is penetrated will become soft and partially dissolved. When the needle is removed from the site of the tissue puncture, a small amount of the gelatin material will remain behind on the margins of the tissue. This small amount of gelatin is quite "sticky" and it will produce adherence of the margins of the tissue so that leakage of blood and/or air does not occur.

Figure 2:
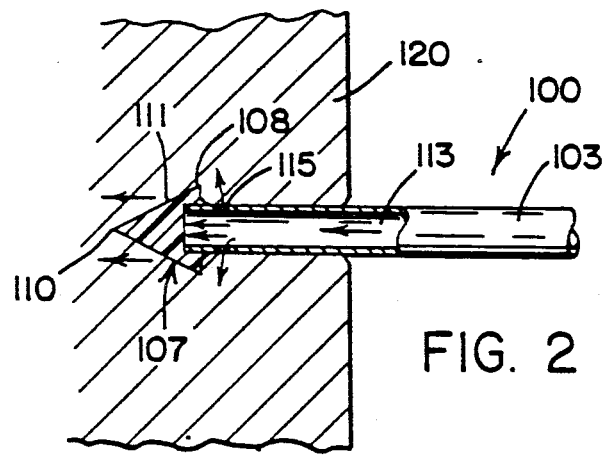
FIG. 2 is a schematic illustration of the needle of FIG. 1 inserted into the tissue of the patient.
Figure 3:
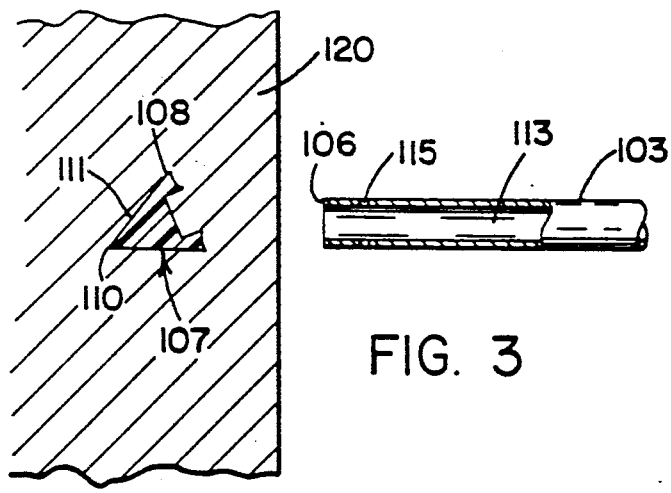
FIG. 3 is a schematic view of the needle of FIG. 1 shown retracted from the patient's tissue after injection.

Referring now to FIGS. 1 through 3, there is schematically illustrated, partially in section, a medical needle 100 and more specifically, a hypodermic needle. Hypodermic needle 100 is conventional in the sense that it includes a conventional syringe 101 in fluid communication with a hollow metal cylinder 103. Hollow metal cylinder 103 has a proximal portion 104 secured to syringe 101 in a conventional manner and a distal portion 106 to which is secured a bioabsorbable gelatin tip 107. Tip 107 has a base portion 108 at one end adjacent distal portion 106 and a cutting end 110 at its opposite end. Base portion 108 has a diameter greater than the outside diameter of hollow metal cylinder 103 and tapers in a frusto conical manner to cutting end 110 and thus resembles in configuration an arrow head. If desired, barb projections such as shown at 72 in FIG. 7 of my prior patent application could be incorporated in the frusto conical surface 111 extending between base portion 108 and cutting end 110. In fact, alternative configurations of gelatin tip 107 structured to fit within hollow metal cylinder 103 so as to be lacking a significant protruding base portion 108 would of necessity require such barbs for reasons which will be explained hereafter. It will be noted that gelatin tip 107 is solid and closes the longitudinal opening 113 in hollow metal cylinder 103 at its distal portion 106. In order to provide means for syringe 101 to draw and inject medication (liquid medium) into and from hypodermic needle 100, small openings 115 are provided in hollow metal cylinder 103 just rearwardly of the tip's base portion 108. Base portion 108 of gelatin tip 107 is sized, both in length and diameter relative to the diameter of hollow metal cylinder 103 to snugly yet securely fit in place. In this connection, it is possible to provide a circular protrusion in the interior of base portion 108 which could snap over a circular groove provided in distal portion 106 of hollow metal cylinder 103 (not shown) to insure attachment. It is also possible, and perhaps preferable, to cast gelatin tip 107 in place and then sharpen cutting end 110 and trim off any "flashing" to produce the appropriate length of base portion 108.

With the detachable gelatin tip 107 of hypodermic needle 100 shown in FIGS. 1 through 3, hypodermic needle 100 would be conventionally inserted into the patient and the medication injected in the routine fashion. As gelatin tip enters tissue 120 and as noted in my prior patent application, body fluids in contact with gelatin tip 107 reduce the coefficient of friction of gelatin tip 107 permitting easy penetration. As syringe 101 is actuated and the medication is injected through cross openings 115, the medication will also exert pressure against gelatin tip 107 and in fact gelatin tip 107 will preferably detach slightly from distal portion 106 of hollow metal cylinder 103. When hypodermic needle 100 is removed, gelatin tip 107 will remain in the patient. This occurs because gelatin tip 107 is broad at base portion 108 and subcutaneous tissue 120 will resist its exit. Gelatin tip 107 being bioabsorbable will dissolve over a period of several days. Once hypodermic needle 100 is removed, it will no longer be "sharp" because the point of the needle has been detached and it is now only a metal cylinder. In this form, hypodermic needle can no longer puncture the skin, either intentionally, so as to prevent the reuse of such needles by drug addicts which might recover same from hospital waste, or unintentionally, in the case of health professionals which might inadvertently be punctured in the handling of used needles. In either event, the end result is the prevention of transmittable diseases of viruses such as AIDS through the blood stream.

An alternative embodiment of hypodermic needle 100 is shown in FIGS. 4 through 7 and reference numerals in FIGS. 1 through 3 will identify like parts and surfaces with respect to hypodermic needle 100 of FIGS. 4 through 7. Gelatin tip 107 in the embodiment of FIGS. 4 through 7 is not removable. With this embodiment, gelatin material is cast onto distal portion 106 and to some extent onto the outside (not shown) of distal portion 106 of hollow metal cylinder 103. An opening 130 is then provided into base portion 108 of tip 107 so that longitudinal opening 113 in hollow metal cylinder 103 remains open through its distal portion 106. When the gelatin material is hardened, it is sharpened to have the cutting end 110 not entirely dissimilar to that of an end cutting biopsy needle such as shown in FIGS. 8 and 9 of my prior patent application. When needle 100, after injection of the medication, is removed from tissue 120, gelatin tip 107 remains attached to hollow metal cylinder 103. Because body fluid and medication diluent is absorbed into distal tip 107 during injection, the cutting end 110 becomes soft and distorted as illustrated in FIG. 7 and no longer is functional as a penetration device. After use, hypodermic needle 100 is dropped into a water bath which further dissolves the tip making the needle unusable in its later form. It should also be noted with respect to the alternative embodiment of FIGS. 4 through 7, that as needle 100 is removed from tissue 120, a small portion of gelatin tip 107 will dissolve as described with reference to the bioabsorbable hemostatic sheath 36 discussed above and a small amount of the material will remain behind on the margins of the tissue punctured by the needle. The stickiness of the gelatin left behind will promote adherence of the margins of the tissue tending to prevent leakage of blood and/or air.

As noted in my prior patent application, the bioabsorbable material discussed herein is made with conventionally available bioabsorbable gelatin with either a pork or a beef base and conventional additives are added to the base material depending on the dissolution time desired for the gelatin material. An acceptable gelatin material is available in a foam or a sponge form from the Upjohn Company under the trademark GEL-FOAM. The GEL-FOAM material would have to be made in hardened form by the means of conventional additives to be used in this invention. An acceptable hardened thiolated gelatin material which could also be used is described in U.S. Pat. No. 3,106,483 dated Oct. 8, 1963 which has been incorporated by reference herein. Also to avoid any confusion in terminology, "bioabsorbable" is used herein in the sense that the gelatin is absorbed by the normal chemical substances and reactions occurring within the body and is equivalent somewhat to the term "biodegradable".

The invention has been described with reference to my prior patent application as a further extension and modification of several of the concepts disclosed therein. One of the essential features of my prior patent application was to avoid hemorrhagic complication resulting from the surgical procedure using a needle or like instrument. In this invention, the avoidance of hemorrhagic complications resulting from the compression of the tissue by an in situ non-bioabsorbable sheath is realized. Further, by this invention, it is realized that a bioabsorbable gelatin sheath need not be deposited in situ to realize the benefits of the gelatin material preventing leakage of air, gas and/or blood from, to or through the puncture site. Finally, and importantly, recognizing the bioabsorbable qualities of the gelatin material, medical needles have been developed which render their sharpened end useless after initial injection to minimize health risks. It is my intention to include all modifications and alterations of the device disclosed herein insofar as they come within the scope of the present invention.

Having thus described my invention, I claim:

1. A biopsy needle for taking a biopsy specimen from a patient, said needle having an unactuated position defined by a relative position of its parts prior to insertion in the patient, an actuated position defined by the relative position of its parts while said specimen is being taken and a retracted position defined by the relative position of its parts when said needle is removed from the site where the biopsy was taken, said needle comprising:
    a) an inner cutting cannula having a distal portion for insertion into said site and a contiguous proximal portion extending from said distal portion, said distal portion defined as the length of said inner cannula which is inserted into said patient in said actuated position, and including means to sever said specimen from said patient;
    b) an outer hollow cannula co-axial with and receiving said inner cannula, said outer cannula having a proximal portion and a separable distal portion, said separable distal portion being separated from said proximal portion and remaining at said site in said retracted position of said needle;
    c) position means associated with said proximal portions of said inner and outer cannulas to cause movement of one of said cannulas relative to the other when said needle moves from one of said positions to the other; and
    d) said separable distal portion of said outer cannula remaining at said site and being sized relative to said inner cannula to compress site tissue thereat for minimizing bleeding or gas escape from said site after said needle is removed from said site.

2. The needle of claim 1 wherein said distal portion of said outer cannula is made of a non-bioabsorbable substance such as teflon and the like.

3. The needle of claim 1 wherein said distal portion of said outer cannula is made of a bioabsorbable gelatin material.

4. The needle of either claims 2 or 3 wherein said distal portion of said outer cannula has an outside diameter greater than said proximal portion of said outer cannula and greater than the initial puncture in said tissue caused by said inner cannula.

5. A biopsy needle for insertion into the subcutaneous tissue of a patient to take a biopsy specimen from a biopsy site within said patient; said biopsy needle having a hollow cylinder, means within said hollow cylinder to sever said specimen from said patient, a cutting edge at the distal end of said cylinder for puncturing and insertion into said tissue and a bioabsorbable gelatin material disposed as a sheath about a portion of said hollow cylinder, means to leave said sheath of bioabsorbable material about the margins of said tissue at the insertion site to improve adhesion of said margins and minimize bleeding when said device is removed from said insertion site after insertion and removal of said specimen from said biopsy site.

* * * * *